(12) United States Patent
Yamamoto et al.

(10) Patent No.: US 10,238,297 B2
(45) Date of Patent: Mar. 26, 2019

(54) OBJECT INFORMATION ACQUIRING APPARATUS

(71) Applicant: CANON KABUSHIKI KAISHA, Tokyo (JP)

(72) Inventors: Hiroshi Yamamoto, Kawasaki (JP); Yukio Furukawa, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 845 days.

(21) Appl. No.: 14/810,567

(22) Filed: Jul. 28, 2015

(65) Prior Publication Data

US 2016/0029895 A1 Feb. 4, 2016

(30) Foreign Application Priority Data

Aug. 4, 2014 (JP) ................................. 2014-158628

(51) Int. Cl.
*A61B 5/00* (2006.01)
*G01N 21/17* (2006.01)
*G01N 21/49* (2006.01)

(52) U.S. Cl.
CPC ....... *A61B 5/0095* (2013.01); *G01N 21/1702* (2013.01); *A61B 5/7221* (2013.01); *A61B 2560/0223* (2013.01); *G01N 21/49* (2013.01)

(58) Field of Classification Search
CPC ................ A61B 5/0095; A61B 5/7221; A61B 2560/0223; G01N 21/1702; G01N 21/49
See application file for complete search history.

(56) References Cited

U.S. PATENT DOCUMENTS

| 5,625,616 A | 4/1997 | Koike et al. .................. 369/116 |
| 5,774,228 A | 6/1998 | Takezawa et al. ............ 356/432 |
| 2008/0123083 A1 | 5/2008 | Wang et al. .................... 356/73 |
| 2011/0106478 A1 | 5/2011 | Someda ........................ 702/104 |
| 2011/0270071 A1 | 11/2011 | Furukawa ..................... 600/407 |
| 2011/0303015 A1 | 12/2011 | Ichihara et al. ................ 73/656 |
| 2012/0033201 A1 | 2/2012 | Fujiwara ........................ 356/51 |

(Continued)

FOREIGN PATENT DOCUMENTS

| CN | 1141505 A | 1/1997 |
| CN | 1175694 A | 3/1998 |

(Continued)

OTHER PUBLICATIONS

Partial European Search Report dated Jan. 5, 2016 in counterpart EP 15176231.7 (in English).

(Continued)

*Primary Examiner* — Peter Luong
(74) *Attorney, Agent, or Firm* — Venable LLP

(57) ABSTRACT

The present invention uses an object information acquiring apparatus having: an optical transmitter that transmits light and emits the light to an object; a first optical meter disposed at the incidence side of the optical transmitter; a second optical meter disposed at the emission side of the optical transmitter; a calculator that calculates an equation that indicates the relationship between the fluence of light measured by the first optical meter and the fluence of light measured by the second optical meter; a probe that receives an acoustic wave that is generated from the object due to the light emitted by the optical transmitter and converts the acoustic wave; and a processor that acquires specific information about the inside of the object.

10 Claims, 5 Drawing Sheets

(56) References Cited

U.S. PATENT DOCUMENTS

| | | | |
|---|---|---|---|
| 2012/0283532 A1 | 11/2012 | Suzuki | 600/322 |
| 2013/0188129 A1 | 7/2013 | Inoue | 351/206 |
| 2013/0231549 A1 | 9/2013 | Yamamoto et al. | 5/95 |
| 2013/0276542 A1 | 10/2013 | Herzog et al. | 73/655 |
| 2013/0331680 A1 | 12/2013 | Furukawa | 5/95 |
| 2014/0064030 A1 | 3/2014 | Yamamoto et al. | A61B 5/0095 |
| 2014/0064040 A1 | 3/2014 | Yamamoto et al. | 5/95 |
| 2014/0194724 A1 | 7/2014 | Ichihara et al. | 5/95 |

FOREIGN PATENT DOCUMENTS

| | | |
|---|---|---|
| CN | 102365049 A | 2/2012 |
| CN | 102596049 A | 7/2012 |
| CN | 102695459 A | 9/2012 |
| CN | 103251378 A | 8/2013 |
| JP | H10(1998)-193146 | 7/1998 |
| JP | 2002-345981 A | 12/2002 |
| JP | 2011-229735 A | 11/2011 |

OTHER PUBLICATIONS

European Extended Search Report issued on Jun. 6, 2016 in counterpart EP 15176231.7 (in English).
Office Action dated Sep. 4, 2017 in counterpart P.R. China application CN 201510457900.3, with translation.
Office Action dated Jul. 24, 2018 in counterpart application JP 2014-158628 (9 pages).

OBJECT INFORMATION ACQUIRING APPARATUS

BACKGROUND OF THE INVENTION

Field of the Invention

The present invention relates to an object information acquiring apparatus.

Description of the Related Art

Photoacoustic tomography (PAT) is one of the methods for obtaining an optical characteristic value (e.g., an absorption coefficient) of the inside of an object such as a living body. When pulsed light that is generated from a light source is radiated to a living body, the light propagates while diffusing through the inside of the living body. A light absorber within the living body absorbs the propagating light and generates a photoacoustic wave. The photoacoustic wave is received by a probe, and this received signal is analyzed, to acquire an initial sound pressure distribution originated from the light absorber of the living body. An absorption coefficient distribution can be obtained from the initial sound pressure distribution by using the following formula (1), where $P_0$ represents the initial sound pressure, $\Gamma$ the Gruneisen coefficient, $\mu_a$ the absorption coefficient, and $\phi$ the fluence of light.

$$\mu_a(r) = P_0(r)/\{\Gamma \cdot \phi(r)\} \quad (1)$$

As is clear from this formula (1), the fluence of light needs to be figured out correctly in order to accurately obtain the absorption coefficient distribution. Unfortunately, it is not easy to directly measure the fluence of light radiated to the object while the object is being measured. Therefore, the fluence of light radiated to the object is measured indirectly based on the outputs of the light source and the transmissivity of the optical components between the light source and the object.

However, since the measurement accuracy of this method drops as the optical components deteriorate, a decline of the transmission efficiency triggered by the deterioration of the optical components needs to be figured out. According to the technique disclosed in Japanese Patent Application Laid-Open No. H10(1998)-193146, part of the fluence of light entering an optical fiber and part of the fluence of light emitted from the optical fiber are measured at all times, and when the ratio therebetween falls below a predetermined value, it is determined that the optical fiber has deteriorated. Such determination is to encourage replacement of the optical fiber so that the transmission efficiency can be kept within a certain range.

Patent Literature 1: Japanese Patent Application Laid-Open No. H10(1998)-193146

SUMMARY OF THE INVENTION

Japanese Patent Application Laid-Open No. H10(1998)-193146, however, does not describe that the result of detecting a deterioration of the optical components such as the optical fiber is reflected in reconstruction of a photoacoustic device. The problem that arises when applying the device disclosed in Japanese Patent Application Laid-Open No. H10(1998)-193146 to a photoacoustic device is that the specific information about the inside of the object cannot be acquired accurately because the fluence of light emitted from the optical fiber is not measured.

The present invention was contrived in view of such problem, and an object thereof is to provide a technique for accurately acquiring the specific information about the inside of an object in view of the transmission efficiency of an optical transmitter of a photoacoustic device.

The present invention provides an object information acquiring apparatus, comprising:

a light source;

an optical transmitter configured to transmit light input from the light source, and emit the light to an object;

a first optical meter disposed at an incidence side of the optical transmitter;

a second optical meter disposed at an emission side of the optical transmitter;

a calculator configured to calculate a conversion factor that indicates a relationship between the fluence of light measured by the first optical meter and the fluence of light measured by the second optical meter;

a probe configured to receive an acoustic wave that is generated from the object due to the light emitted by the optical transmitter and convert the acoustic wave into an electric signal; and a processor configured to acquire specific information about the inside of the object based on the electric signal, wherein the processor:

acquires the fluence of the light emitted by the optical transmitter based on the conversion factor calculated by the calculator and the fluence of light measured by the first optical meter; and acquires the specific information based on the electric signal and the fluence of the light emitted by the optical transmitter.

The present invention also provides an object information acquiring apparatus, comprising:

a light source;

an optical transmitter configured to transmit light input from the light source, and emits the light to an object;

a first optical meter disposed at an incidence side of the optical transmitter;

a storage configured to store a conversion factor that indicates a relationship between the fluence of light measured by the first optical meter and the fluence of the light emitted from the optical transmitter;

a probe configured to receive an acoustic wave that is generated from the object due to the light emitted by the optical transmitter and converts the acoustic wave into an electric signal; and a processor configured to acquire specific information about the inside of the object based on the electric signal, wherein the processor:

calculates the fluence of the light emitted by the optical transmitter based on the conversion factor stored in the storage and the fluence of light measured by the first optical meter; and acquires the specific information based on the electric signal and the fluence of the light emitted by the optical transmitter.

Further features of the present invention will become apparent from the following description of exemplary embodiments with reference to the attached drawings.

DESCRIPTION OF THE EMBODIMENTS

Figure 1A:
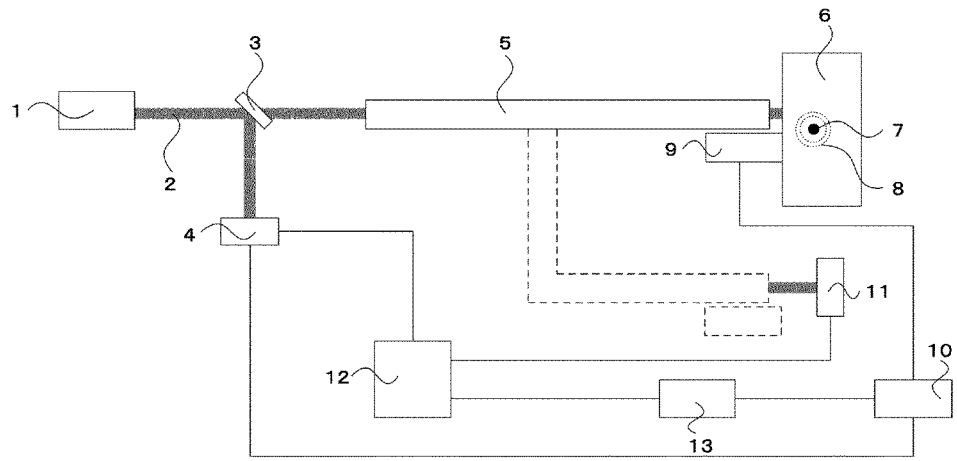
FIGS. 1A and 1B are each a configuration diagram of a photoacoustic device of Example 1.

Preferred embodiments of the present invention are now described hereinafter with reference to the drawings. However, the sizes, materials, shapes and relative arrangement of the components described below are to be changed appropriately based on the configurations of the devices to which the present invention is applied and various conditions, and are not intended to limit the scope of the present invention to the following descriptions.

The present invention pertains to a technique for detecting an acoustic wave propagating from an object, and generating and acquiring the specific information about the inside of the object. The present invention, therefore, is considered as an object information acquiring apparatus, a method for controlling the same, an object information acquisition method, and a signal processing method. The present invention is also considered as a program that causes an information processing device with a CPU and other hardware resources to execute these methods, and a storage medium storing this program. The present invention is also considered as an acoustic wave measuring device or a method for controlling the same.

The object information acquiring apparatus according to the present invention includes a device using photoacoustic tomography, which radiates light (an electromagnetic wave) to an object and receives (detects) an acoustic wave that is generated at a specific position on the inside of the object or on the surface of the object and propagates by the photoacoustic effect. Such object information acquiring apparatus can be referred to as "photoacoustic imaging device" or "photoacoustic image-forming apparatus," because it obtains the specific information about the inside of the object in the form of image data or the like by means of photoacoustic measurement. The object information acquiring apparatus of the present invention may also be simply referred to as "photoacoustic device."

The specific information obtained by the photoacoustic device indicates a distribution of the sources of acoustic waves generated by radiation of light, an initial sound pressure distribution of the inside of the object, an optical energy absorption density distribution or absorption coefficient distribution that can be derived from the initial sound pressure distribution, and a distribution of the concentrations of the substances constituting the tissues. Specifically, the specific information includes blood component distributions such as oxidized/reduced hemoglobin concentration distributions and an oxygen saturation distribution that can be obtained therefrom, or distributions of the fat, collagen, and moisture content. In addition, the specific information may be obtained not as numeric data but as distribution information on various positions inside the object. In other words, the distribution information on the absorption coefficient distribution and oxygen saturation distribution may be acquired as object information.

Acoustic waves described in the present invention are typically ultrasonic waves, including elastic waves called "sound waves" or "acoustic waves." Acoustic waves generated by the photoacoustic effect are called "photoacoustic waves" or "optical ultrasonic waves." An electric signal converted from an acoustic wave by a probe is called "acoustic signal," and an acoustic signal originated from a photoacoustic wave is called "photoacoustic signal."

A breast of a living body can be considered as the object described in the present invention. However, the object is not limited thereto; thus, other segments of the living body or a material other than a living body can be measured as well.

<Photoacoustic Device>

First, the basic configuration of a photoacoustic device according to each of the embodiments of the present invention is described. The photoacoustic device has basic hardware configurations such as a light source, an optical transmitter, a first optical meter, a second optical meter, a calculator, a storage, a probe for receiving photoacoustic waves generated inside the object, and a reconstructor for reconstructing the information about the inside of the object by using a signal received by the probe. The first optical meter measures part of the fluence of light at an area closer to the light source than the incidence end of the optical transmitter. The second optical meter measures the fluence of light radiated to the object.

Part of pulsed light emitted from the light source is guided to the first optical meter and the rest is guided to the incidence end of the optical transmitter. This measured value of the pulsed light is the fluence of light obtained at the incidence side. The light emitted from the optical transmitter is guided to the object when the object is measured. When measuring the fluence of light radiated to the object, on the other hand, the emitted light is guided to the second optical meter. This measured value is the fluence of light obtained at the emission side. Whether to guide the light emitted from the optical transmitter to the object or to the second optical meter is determined automatically or manually.

When the emitted light is guided to the second optical meter, the measured value of the first optical meter and the measured value of the second optical meter are sent to the calculator. The measured value of the second optical meter is deemed to be equivalent to the fluence of light radiated to the object, and a conversion factor for converting the measured value of the first optical meter to the fluence of light radiated to the object is calculated. The resultant conversion factor is stored in the storage.

When, on the other hand, the emitted light is radiated to the object, this light diffuses and propagates through the inside of the object. Part of the energy of the propagating light is absorbed by a light absorber such as blood (which eventually becomes the sound source), and consequently thermal expansion of the light absorber takes place, generating a photoacoustic wave. The photoacoustic wave generated inside the object is received by the probe. The signal received by the probe is transmitted to the reconstructor. The reconstructor reconstructs the information about the inside of the object from the signal transmitted from the probe, the measured value of the first optical meter used for measuring the object, and the conversion factor stored in the storage, and then acquires the specific information about the inside of the object.

(Light Source)

In a case where the object is a living body, the light source radiates pulsed light of a certain wavelength that is absorbed by a specific component out of the components configuring the living body. In the present invention, a wavelength that enables propagation of the light deep into the object is preferably used. Specifically, in a case where the object is a living body, the wavelength is 600 nm or higher and 1100 nm or lower. It is preferred that the pulse width be approximately 10 to 100 nanoseconds for the purpose of effectively generating a photoacoustic wave. It is preferred that the light source be a laser for its ability to obtain large outputs, but a light-emitting diode, a flashlamp or the like can also be used in place of the laser. Various lasers such as a solid-state laser, a gas laser, a dye laser, and a semiconductor laser can be used as the laser. The timing, waveform, intensity and the like of radiation are controlled by a light source controller. Note that this light source controller may be integrated with the light source.

(Optical Transmitter)

The optical transmitter can be an optical transmitter that performs transmission of light using an optical fiber, transmission of light using an articulated arm with a plurality of mirrors or prisms, space transmission using a lens, a mirror, a prism, or a diffuser, or a combination of these transmission methods. In a case where an acoustic matching member such as water or ultrasonic gel is present in an optical transmission path, the acoustic matching member may be included in the optical transmitter.

(Object and Light Absorber)

Although neither the object nor the light absorber configures a part of the photoacoustic device of the present invention, these will be described hereinafter. The photoacoustic device of the present invention utilizing the photoacoustic effect mainly aims to image a blood vessel, diagnose malignant tumors or vascular diseases in a human or animal, and observe the process of the chemotherapy for these diseases. The light absorber on the inside of the object has a relatively high absorption coefficient in the object, depending on the wavelength of the light used. Specific examples of the light absorber include water, fat, protein, oxidized hemoglobin, and reduced hemoglobin.

By retaining the object using a plate-like or hemispherical (spherical crown-shaped) retaining member, the living body can be kept still, enabling stable measurement thereof. The retaining member is preferably made of material that transmits at least acoustic waves, and is required to be optically transmissive in order to radiate light to the object through the retaining member.

(Probe)

The probe has a transducer that receives a photoacoustic wave that is generated in the surface of the living body or on the inside of the living body and converts the photoacoustic wave into an electric signal (analog signal). The transducer may be a transducer for a PZT or the like using a piezoelectric phenomenon, a transducer that uses a Fabry-Perot interferometer or the like employing an optical resonance, a transducer that uses a CMUT or the like for detecting changes in electrostatic capacity using the MEMS technology, or any other transducer capable of receiving acoustic waves. The surface of the probe may be provided with a gold film or a reflecting film for sending the light that is reflected off the surface of the object or of the retaining member for the object or the light that scatters inside the object and comes out of the object, back to the object again.

By measuring the object while moving the probe using a scan controller described below, it is possible to detect a photoacoustic wave from a wide range. In so doing, the probe may be moved in synchronization with the light emission end of the light source. Moreover, by arranging a plurality of lines of transducers two-dimensionally or three-dimensionally, not only is it possible to reduce the time it takes for the measurement, but also the SN ratio can be improved.

When retaining the object with the hemispherical (spherical crown-shaped) retaining member as described above, it is preferred that each of the transducers of the probe be disposed in a support, which is also in the shape of a hemisphere (spherical crown), so that a high-sensitivity region, in which a uniform angular range (directional axis) where the transducers have high reception sensitivities is obtained, can be provided. Such support can support the plurality of transducers in such a manner that the direction in which the reception sensitivities of at least some of the plurality of transducers are high is different from the direction in which the reception sensitivities of transducers other than the at least some of the plurality of transducers are high, and is directed toward a specific region.

In a case where the probe is smaller than a measurement target, the probe may be caused to scan the target to receive acoustic waves at a plurality of positions. The acoustic waves received by the probe are converted into electric signals and subjected to amplification and digital conversion by a signal processing circuit, if necessary. Subsequently, the resultant signals are used to create the specific information in the processor.

(First Optical Meter)

The first optical meter measures part of the fluence of the pulsed light emitted from the light source. The first optical meter may measure part of the fluence of the light entering the optical transmitter. In a case where the light source is a laser, the first optical meter may measure the fluence of light transmitted through a rear mirror.

(Second Optical Meter)

The second optical meter measures the fluence of light radiated to the object. The second optical meter may be installed in the photoacoustic device at all times or may be detachable through a connector. A configuration is possible in which part of the light emitted from the optical transmitter is measured using the second optical meter to estimate the whole fluence of light.

Various existing actinometers capable of acquiring the fluence of optical energy per unit time can be used as the first optical meter and the second optical meter. For example, a photoelectronic device that converts the fluence of incident light into a current intensity, a device using a semiconductor, a device using an optical element, an actinometer using a photochemical reaction, and the like can be used.

(Calculator)

The calculator calculates a conversion factor for converting the measured value of the first optical meter into the fluence of light radiated to the object, by using the measured value of the first optical meter and the measured value of the second optical meter. The conversion factor may be a constant or a polynomial of degree n (n being an integer of 1 or more). In a case where it is difficult to measure the fluence of light radiated to the object due to close contact between the object and the plate-like retaining member or due to the presence of the object in an acoustic matching member such as water, the conversion factor may be calculated based on the value measured in the air by the second optical meter in consideration of the Fresnel loss that occurs in the member interface or the light absorption loss that occurs within the member.

The calculator typically has a CPU and a memory and is realized by an information processing device (a PC, a workstation, etc.) that executes an arithmetic process in accordance with a predetermined program. The components of the information processing device may be integrated or may be connected with one another by a network and operated in cooperation with each other.

(Storage)

The storage stores the conversion factor calculated by the calculator. The stored conversion factor is sent to the reconstructor and used for reconstruction of the object information. A memory or storage device capable of saving information can be used as the storage. Examples of the storage include a RAM, a ROM, a hard disk, and an SSD. When configuring the calculator or reconstructor with an information processing device, a storage device that is provided on the inside of the information processing device or connected on the outside of the information processing device is favorably used as the storage.

(Reconstructor)

The reconstructor creates data related to optical characteristic value distribution information about the inside of the object from the signal received by the probe. Examples of such data include an initial sound pressure distribution of acoustic waves generated as a result of radiation of the light to the object. For example, a time-domain back-projection method can be used to create an optical characteristic value distribution.

The reconstructor can be configured with an information processing device that is operated in accordance with a program and has computational resources such as a CPU and a memory, as with the calculator. Dedicated arithmetic circuits may be used as the reconstructor and the calculator. The reconstructor corresponds to the processor of the present invention.

EXAMPLE 1

Figure 1B:
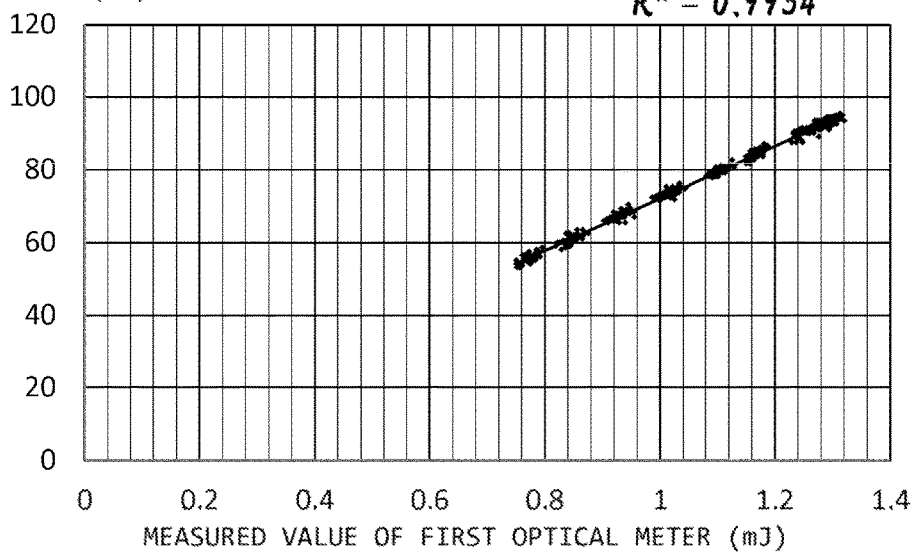

The configuration of Example 1 is described with reference to FIGS. 1A and 1B. FIG. 1A is a configuration diagram of the present example. FIG. 1B is a diagram for explaining a method for calculating the conversion factor in the present example.

In FIG. 1A, reference numeral 1 represents the light source, 2 light, 3 a light divider, 4 the first optical meter, 5 the optical transmitter, 6 the object, 7 the light absorber, and 8 a photoacoustic wave. In addition, reference numeral 9 represents the probe, 10 the reconstructor, 11 the second optical meter, 12 the calculator, and 13 the storage.

A titanium-sapphire laser is used as the light source 1. The titanium-sapphire laser has a wavelength of 756 nm, produces an output of 120 mJ per pulse, and has a repetitive pulse frequency of 10 Hz and a pulse width of 20 nanoseconds. The light 2 emitted from the light source is partially divided by the light divider 3, and is guided to the first optical meter 4. The percentage of the light divided by the light divider 3 is 1.1%. The light 2 that is transmitted through the light divider 3 is transferred to the optical transmitter 5 and, for measurement of the object 6, radiated to the object 6. A bundle of a plurality of optical fibers is used as the optical transmitter 5.

The light that diffuses inside the object 6 is absorbed by the light absorber 7. Consequently, the photoacoustic wave 8 is generated from the light absorber 7 and received by the probe 9. A piezoelectric material such as lead zirconate titanate (PZT) is used as the probe 9. The emission end of the optical transmitter 5 is integrated with the probe 9. The signal received by the probe 9 is transmitted to the reconstructor 10.

On the other hand, when measuring the fluence of light radiated to the object 6, the light emitted from the optical transmitter 5 is guided to the second optical meter 11. At this moment, the measured value of the first optical meter 4 and the measured value of the second optical meter 11 are sent to the calculator 12. The calculator 12 considers the measured value of the second optical meter 11 as the fluence of light radiated to the object 6. Then, the calculator 12 performs a calculation using the measured value of the second optical meter 11 and the measured value of the first optical meter 4, to acquire an equation showing the relationship between the fluence of light that is emitted from the light source but has not yet entered the optical transmitter 5 and the fluence of light radiated to the object 6. This calculation is the same as calculating the conversion factor for converting the measured value of the first optical meter 4 into the fluence of light radiated to the object 6.

The calculated conversion factor is stored in the storage 13. The reconstructor 10 reconstructs the information about the inside of the object 6 by using the signal received by the probe 9, the measured value of the first optical meter 4 obtained during the measurement of the object 6, and the conversion factor stored in the storage 13.

The method for calculating the conversion factor using the calculator 12 is now described. FIG. 1B is a diagram in which the horizontal axis shows the measured value of the first optical meter 4 and the vertical axis shows the measured value of the second optical meter 11, the measured values of the optical meters being plotted with respect to the pulses. Measurement is carried out, with the output of the light source 1 being changed by changing the power supplied to the light source 1. As shown in FIG. 1B, the relationship between the measured value x of the first optical meter 4 and the measured value y of the second optical meter 11 (the fluence of light radiated to the object) is obtained in the form of a linear function using a least-squares method. As a result, a conversion factor "$y=71.9x+0.2$" (the equation showing the relationship between the measured values) is obtained.

This conversion factor is stored in the storage 13. When this stored conversion factor is used to reconstruct the object information, the reconstructor calculates the fluence of light radiated to the object 6 by multiplying the fluence of light measured by the first optical meter 4 during the measurement of the object by the conversion factor. The reconstructor 10 also reconstructs the absorption coefficient distribution of the inside of the object 6 based on the calculated fluence of radiated light and the signal received by the probe 9.

In the present example, as described above, part of the fluence of light entering the optical transmitter is measured by the first optical meter, and then the calculator calculates the conversion factor from this measured value and the measured value of the second optical meter incorporated in the photoacoustic device. The use of this conversion factor enables reflection of fluctuations of the transmission efficiency, which occur due to deterioration or replacement of the optical transmitter, in the measurement of the object. For this reason, the fluence of light radiated to the object can be measured accurately and reflected in information reconstruction, so that the specific information about the inside of the object can be acquired accurately.

In the present example, although the conversion factor is calculated by plotting the measurement results of the first and second optical meters with respect to the pulses, the conversion factor may be calculated by plotting the average of a plurality of pulses. Further, in the present example, although the measured value of the first optical meter directly indicates the fluence of light, the measured value may be the current value or voltage value corresponding to the fluence of light.

EXAMPLE 2

Figure 2:
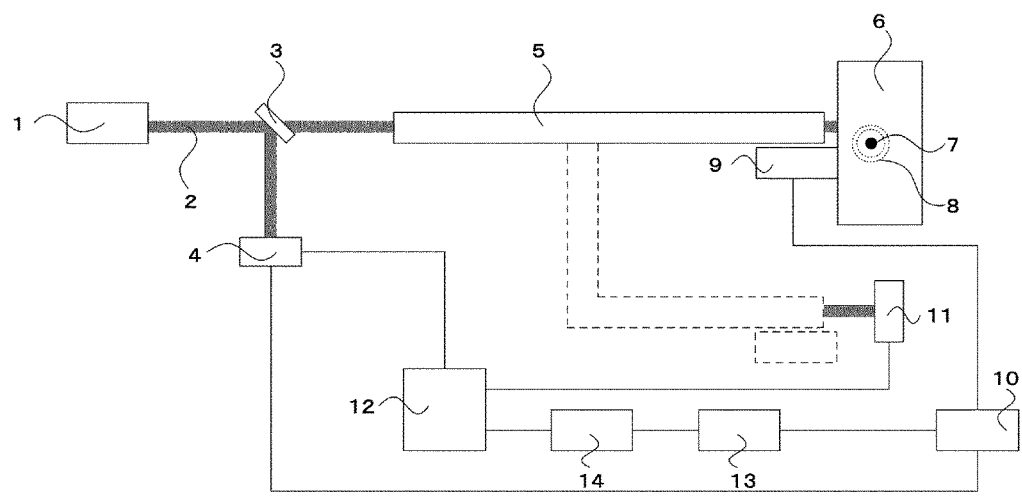
FIG. 2 is a configuration diagram of a photoacoustic device of Example 2.

The configuration of Example 2 is now described with reference to FIG. 2. In FIG. 2, reference numeral 14 represents a determiner. The determiner 14 compares the conversion factor stored in the storage 13 with a new conversion factor calculated by the calculator 12, to determine whether to update the former conversion factor with the latter conversion factor or not. In the present example, when the new conversion factor calculated by the calculator 12 fluctuates by ±3% or more as compared to the conversion factor stored in the storage 13, the determiner 14 determines to update the conversion factor, and updates the conversion factor stored in the storage 13. When the reconstructor 10 reconstructs the information about the inside of the object 6, the reconstructor 10 multiplies the fluence of light measured by the first optical meter 4 during the measurement of the object 6 by the conversion factor, to calculate the fluence of light radiated to the object 6. The reconstructor 10 also reconstructs the absorption coefficient distribution of the inside of the object 6 based on the calculated fluence of radiated light and the signal received by the probe 9.

In the present example, as described above, when the conversion factor that is calculated from the measured value of the first optical meter and the measured value of the second optical meter fluctuates by a predetermined value or higher with respect to a reference value, the conversion factor is updated. This can curb the impact of the fluctuations of the transmission efficiency on a measurement error of the object information within a certain range, the fluctuations occurring due to deterioration or replacement of the optical transmitter.

The standards for determination by the determiner may freely be set by the manufacturer, administrator, user or the like of the device in view of the safety of the device or the like. Not only the threshold of the standards for determination but also the timing of determination can be set freely. In other words, the timing of determination includes, for instance, when the device is manufactured, before the device is shipped, regularly-scheduled inspections and corrections after installation of the device, and when the measurement is performed.

[Modification]

In addition, it is preferred that a problem of some sort that occurs in the obtained conversion factor be dealt with. An abnormal value of the conversion factor in this case is, for example, a value outside a conceivable error range with respect to the set value or a value outside a range that can be expected from the configuration of the device. Moreover, when a conversion factor that was measured in advance is saved in the memory, and when a newly measured conversion factor fluctuates by a predetermined threshold or more in relation to the aforementioned saved conversion factor, it is considered that the abnormal value has occurred. The abnormal value of the conversion factor is suspected to cause a deterioration or malfunction of a component such as the optical transmitter. Therefore, preferably, a notifier is provided in order to notify the user of such deterioration or malfunction. Examples of the notifier include a console integrated with the device, a display device such as a liquid crystal display to be provided outside the device, and sound outputting means such as an alarm.

EXAMPLE 3

Figure 3A:
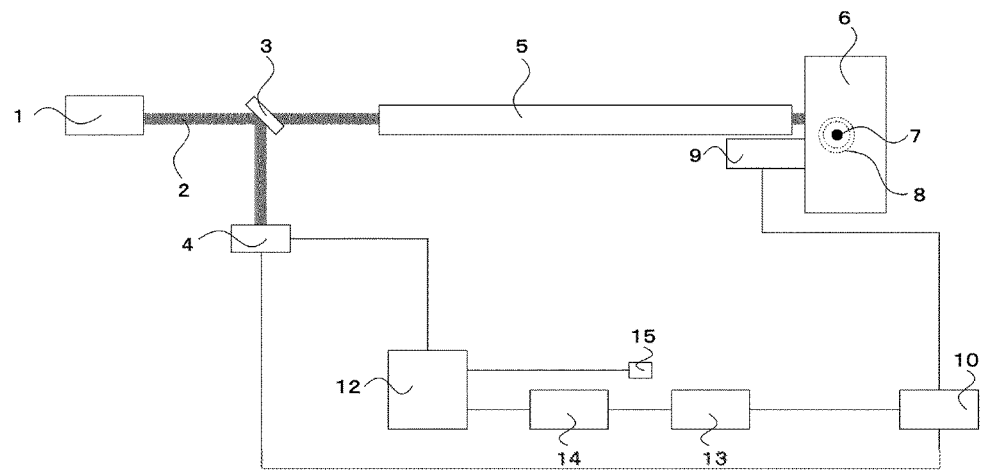
FIGS. 3A and 3B are each a configuration diagram of a photoacoustic device of Example 3.
Figure 3B:
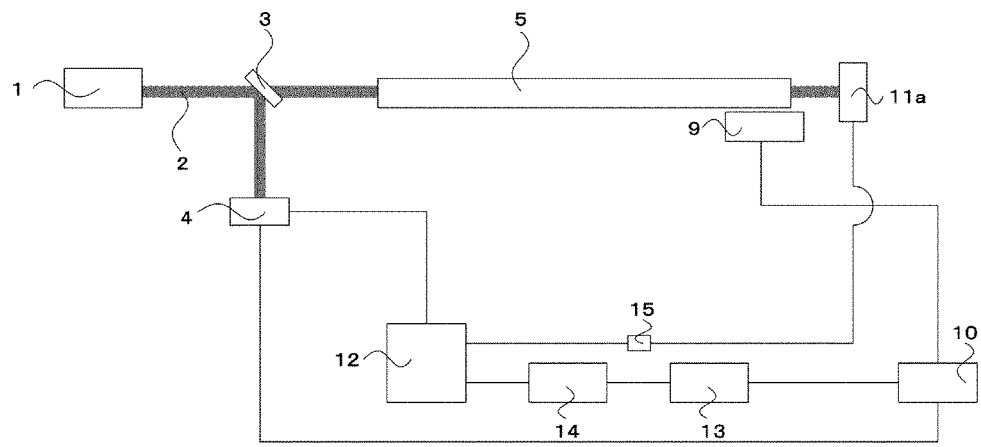

The configuration of Example 3 is now described with reference to FIGS. 3A and 3B. FIG. 3A shows how the object 6 is measured. FIG. 3B shows how the fluence of light emitted from the optical transmitter 5 is measured. In FIGS. 3A and 3B, reference numeral 15 represents a connector. In FIG. 3B, reference numeral 11a represents the second optical meter.

The second optical meter 11a is connected to the calculator 12 by the connector 15. When light is radiated to the object, the second optical meter 11a can be removed from the calculator 12, as shown in FIG. 3A. When measuring the fluence of light emitted from the optical transmitter 5, the second optical meter 11a is connected to the calculator 12 by the connector 15, as shown in FIG. 3B. In this case, the measured value of the first optical meter 4 and the measured value of the second optical meter 11a are sent to the calculator 12.

The calculator 12 considers the measured value of the second optical meter 11a as the fluence of light radiated to the object 6. Through a calculation using the measured value of the second optical meter 11a and the measured value of the first optical meter 4, an equation showing the relationship between the fluence of light that is emitted from the light source but has not yet entered the optical transmitter 5 and the fluence of light radiated to the object 6 can be acquired. This calculation is the same as calculating the conversion factor from the both measured values.

In a case where a new conversion factor calculated by the calculator 12 fluctuates by a predetermined value or more in relation to the conversion factor stored in the storage 13, the determiner 14 determines to update the conversion factor, and the updated conversion factor is then stored in the storage 13. In so doing, the notifier may notify the user of the fact that there is a change to a level that the conversion factor needs to be updated.

When the reconstructor 10 reconstructs the information about the inside of the object 6, the reconstructor 10 multiplies the fluence of light measured by the first optical meter 4 during the measurement of the object 6 by the updated conversion factor, to calculate the fluence of light radiated to the object 6. In a case where the equation showing the relationship between the measured values is not a simple multiplication, then a calculation may be performed in accordance with the equation. The reconstructor 10 also reconstructs the absorption coefficient distribution of the inside of the object 6 based on the calculated fluence of radiated light and the signal received by the probe 9.

As described above, making the second optical meter detachable from the photoacoustic device can eliminate the need to incorporate in the photoacoustic device the means for measuring the fluence of light radiated to the object. The present example, therefore, has the advantage that the size of the photoacoustic device can be reduced.

The present example can be applied in one aspect in which a maintenance personnel such as a manufacturer inspects the device on a regular basis. The maintenance personnel uses the second optical meter that he/she brings with him/her, to determine the presence of a deterioration of the optical transmitter, and replaces the optical transmitter if it is deteriorated.

EXAMPLE 4

Figure 4:
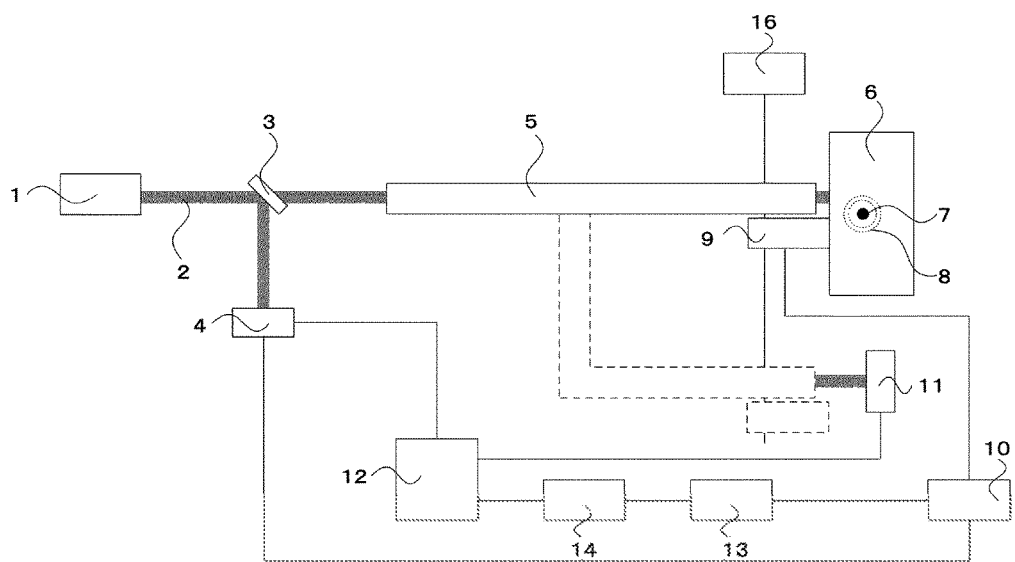
FIG. 4 is a configuration diagram of a photoacoustic device of Example 4.

The configuration of Example 4 is now described with reference to FIG. 4. In FIG. 4, reference numeral 16 represents a scan controller. The scan controller 16 has a stage mechanism and scans the emission end of the optical transmitter 5 and the probe 9 integrally. When measuring the object 6, the emission end of the optical transmitter 5 and the probe 9 are moved to the front of the object 6 by the scan controller 16 in a first scanning mode. When measuring the fluence of light radiated to the object, the emission end of the optical transmitter 5 and the probe 9 are moved to the front of the second optical meter 11 by the scan controller 16 in a second scanning mode.

The calculator 12 considers the measured value of the second optical meter 11 as the fluence of light radiated to the object 6, and calculates the conversion factor for converting the measured value of the first optical meter 4 into the fluence of light radiated to the object 6. The calculated conversion factor is stored in the storage 13. The reconstructor 10 reconstructs the absorption coefficient distribution of the inside of the object 6 based on the signal received by the probe 9, the measured value of the first optical meter 4 obtained during the measurement of the object 6, and the conversion factor stored in the storage 13.

By causing the scan controller to scan the emission end of the optical transmitter and automatically measuring the fluence of light radiated to the object by means of the second optical meter incorporated in the photoacoustic device as described above, the measurement of the object and the measurement of the fluence of light radiated to the object can be performed automatically. The present example, therefore, has the advantage that the burden on the operator of the device can be reduced.

EXAMPLE 5

Figure 5:
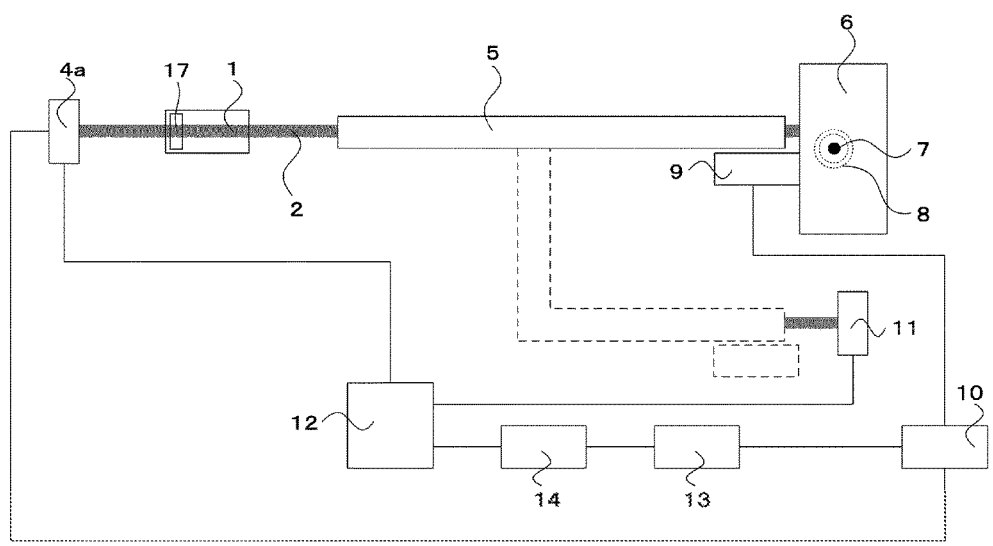
FIG. 5 is a configuration diagram of a photoacoustic device of Example 5.

The configuration of Example 5 is now described with reference to FIG. 5. In FIG. 5, reference numeral 17 represents a rear mirror of a resonator of the light source 1. The fluence of light transmitted through the rear mirror is measured by a first optical meter 4$a$. The measured value of the first optical meter 4$a$ is sent to the calculator 12, and the calculator 12 calculates a conversion factor from the measured value of the first optical meter 4$a$ and the measured value of the second optical meter 11. The calculated conversion factor is stored in the storage 13. The reconstructor 10 reconstructs the absorption coefficient distribution of the inside of the object 6 based on the signal received by the probe 9, the measured value of the first optical meter 4$a$ obtained during the measurement of the object 6, and the conversion factor stored in the storage 13.

As described above, by using the first optical meter to measure the fluence of light transmitted through the rear mirror of the resonator of the laser which is the light source, it becomes unnecessary to provide the light divider separately from the light source. The present example, therefore, has the advantage that the size of the photoacoustic device can be reduced. Due to the absence of the light divider between the light source and the optical transmitter, the present example, unlike Examples 1 to 4, has the advantage that more light can be radiated to the object and the intensity of the signal received by the probe can be increased.

[Modification]

Each of the foregoing examples has described that the second optical meter is either equipped in the device at all times or attached to the device at the time of use. Furthermore, the fluence of light emitted from the optical transmitter is measured based on the measurement result of the second optical meter. However, even without the second optical meter, by storing the conversion factor (relational expression) in the storage device serving as the storage, the specific information about the inside of the object can be acquired based on the fluence of light measured by the first optical meter, the conversion factor, and the electric signal. In this case, the conversion factor may be updated using the detachable second optical meter described in Example 3.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-158628, filed on Aug. 4, 2014, which is hereby incorporated by reference herein in its entirety.

What is claimed is:

1. An object information acquiring apparatus comprising:
   a light source;
   an optical transmitter configured to transmit light emitted from the light source;
   a scan controller configured to move an emission side of the optical transmitter;
   a first optical meter disposed at an incidence side of the optical transmitter and configured to measure light fluence;
   a second optical meter configured to measure light fluence;
   a calculator configured to calculate a conversion factor that indicates a relationship between the fluence of light measured by the first optical meter and the fluence of light measured by the second optical meter;
   a probe configured to receive an acoustic wave that is generated from an object due to the light emitted by the optical transmitter and convert the acoustic wave into an electric signal; and
   a processor configured to acquire specific information about the inside of the object based on the electric signal,
   wherein the scan controller can execute a first scanning mode for moving the optical transmitter so that the optical transmitter irradiates the object with the light emitted from the light source and a second scanning mode for moving the optical transmitter so that the second optical meter measures the fluence of light emitted from the optical transmitter;
   wherein the calculator calculates the conversion factor based on the fluence of light measured by the first optical meter and the fluence of light measured by the second optical meter in the second scanning mode, and wherein the processor acquires the specific information based on the electric signal acquired by the probe in the first scanning mode, the fluence of light measured by the first optical meter in the first scanning mode, and the conversion factor.

2. The object information acquiring apparatus according to claim 1, further comprising a storage configured to store the conversion factor calculated by the calculator.

3. The object information acquiring apparatus according to claim 2, further comprising a determiner configured to compare the conversion factor stored in the storage with a new conversion factor calculated by the calculator, and update the conversion factor stored in the storage to the new conversion factor calculated by the calculator when the variation of conversion factor is included within a predetermined range.

4. The object information acquiring apparatus according to claim 1, further comprising a determiner configured to determine whether the conversion factor is included within a predetermined range or not.

5. The object information acquiring apparatus according to claim 3, wherein the determiner is configured to cause a notifier to issue a notification of the fact that the conversion factor is beyond the predetermined range.

6. The object information acquiring apparatus according to claim 1, further comprising a connector configured to detachably connect the second optical meter to the calculator.

7. The object information acquiring apparatus according to claim 1, further comprising an optical divider configured to divide part of the light of the light source,
wherein the first optical meter measures the fluence of light divided by the optical divider.

8. The object information acquiring apparatus according to claim 1, wherein the processor:
acquires the fluence of light emitted from the optical transmitter in the first scanning mode based on the fluence of light measured by the first optical meter and the conversion factor, and
acquires the specific information based on the electric signal acquired in the first scanning mode with the probe, and, the fluence of light emitted from the optical transmitter in the first scanning mode.

9. An object information acquiring method comprising:
a first optical measurement step of measuring fluence of light which has been emitted from a light source at an incidence side of an optical transmitter;
a second optical measurement step of measuring fluence of light emitted from the optical transmitter;
a scanning step of moving an emission side of the optical transmitter;
a calculating step of calculating a conversion factor that indicates a relationship between the fluence of light measured by the first optical measurement step and the fluence of light measured by the second optical measuring step;
a conversion step of receiving an acoustic wave that is generated from the object due to the light emitted by the optical transmitter and converting the acoustic wave into an electric signal; and
a processing step of acquiring specific information about the inside of the object based on the electric signal,
wherein the scanning step includes:
a first scanning sub-step of moving the optical transmitter so that the optical transmitter irradiates the object with the light emitted from the light source, and
a second scanning sub-step of moving the optical transmitter so that the fluence of light emitted from the optical transmitter is measured in the second optical measurement step,
wherein the calculating step calculates the conversion factor based on the fluence of light measured in the first optical measurement step in the second scanning sub-step and the fluence of light measured in the second optical measurement step in the second scanning sub-step, and
wherein the processing step acquires the specific information based on, the electric signal acquired in the first scanning sub-step, the fluence of light measured in the first optical measurement step in the first scanning sub-step, and the conversion factor.

10. A non-transitory computer-readable storage medium storing a program causing a computer to execute an object information acquiring method comprising:
a first optical measurement step of measuring fluence of light which has been emitted from a light source at an incidence side of an optical transmitter;
a second optical measurement step of measuring fluence of light emitted from the optical transmitter;
a scanning step of moving an emission side of the optical transmitter;
a calculating step of calculating a conversion factor that indicates a relationship between the fluence of light measured by the first optical measurement step and the fluence of light measured by the second optical measuring step;
a conversion step of receiving an acoustic wave that is generated from the object due to the light emitted by the optical transmitter and converting the acoustic wave into an electric signal; and
a processing step of acquiring specific information about the inside of the object based on the electric signal,
wherein the scanning step includes:
a first scanning sub-step of moving the optical transmitter so that the optical transmitter irradiates the object with the light emitted from the light source, and
a second scanning sub-step of moving the optical transmitter so that the fluence of light emitted from the optical transmitter is measured in the second optical measurement step,
wherein the calculating step calculates the conversion factor based on the fluence of light measured in the first optical measurement step in the second scanning sub-step and the fluence of light measured in the second optical measurement step in the second scanning sub-step, and
wherein the processing step acquires the specific information based on, the electric signal acquired in the first scanning sub-step, the fluence of light measured in the first optical measurement step in the first scanning sub-step, and the conversion factor.

* * * * *